(12) United States Patent
Shigemori et al.

(10) Patent No.: US 7,022,501 B1
(45) Date of Patent: Apr. 4, 2006

(54) LIGATION OF DOUBLE-STRANDED DNAS

(75) Inventors: Yasushi Shigemori, Chiba (JP); Michio Oishi, Tokyo (JP)

(73) Assignee: Aisin Seiki Kabushiki Kaisha, Aichi (JP)

( * ) Notice: Subject to any disclaimer, the term of this patent is extended or adjusted under 35 U.S.C. 154(b) by 0 days.

(21) Appl. No.: 09/607,361

(22) Filed: Jun. 30, 2000

(30) Foreign Application Priority Data

Jul. 2, 1999 (JP) ................................. 11-189211

(51) Int. Cl.
| | |
|---|---|
| C12P 19/34 | (2006.01) |
| C12P 21/06 | (2006.01) |
| C12N 15/64 | (2006.01) |
| C12N 9/00 | (2006.01) |
| C22N 1/20 | (2006.01) |

(52) U.S. Cl. ................. 435/91.1; 435/69.1; 435/91.42; 435/252.3; 435/183

(58) Field of Classification Search ................ 435/455, 435/6, 91.1, 91.53, 69.1, 91.42, 252.3, 183
See application file for complete search history.

(56) References Cited

U.S. PATENT DOCUMENTS 5,460,941 A * 10/1995 Camerini-Otero et al.
6,541,226 B1    4/2003 Shigemori et al.

FOREIGN PATENT DOCUMENTS

WO    WO97/04111    2/1997
WO    WO-97/04111  * 2/1997

OTHER PUBLICATIONS

R. Daniel Camerini-Otero et al. Homologous Recombination Proteins in Prokaryotes and Eukaryotes Annu. Rev. Genetics 1995 29:509-52.*
John G. K. Williams et al. *Escherichia coli* RecA Protein Protects Single-stranded DNA of Gapped Duplex DNA from Degradation by RecBC DNase* The Journal of Biological Chemistry vol. 256 No. 14 Jul. 25, pp. 7573-7582 1981.*
Fujiwara et al., Direct cloning by covalent attachment of probe DNA to target DNA, 1998, Nucleic Acids Research, vol. 26, pp. 5734-5737.*
Fujiwara et al., Direct probing: covalent attachment of porbe DNA to double-stranded target DNA, Nucleic Acids Research, vol. 26, pp. 5728-5733.*
Cimmino et al., Ligation of nonmatching DNA molecule ends, 1995, PLASMID, vol. 34, pp. 1-10.*
Fujiwara et al., *Nucleic Acids Research*, 26(24):5734-5737 (1998).
Fujiwara et al., *Nucleic Acids Research*, 26(24):5728-5733 (1998).
Aslanidis et al., *Nucleic Acids Research*, 18(20):6069-6074 (1990).
Martin Teintze, *RecA-Assisted Rapid Enrichment of Specific Clones from Model Dna Libraries*, Biochemical and Biophysical Research Communications, 211(3): 804-811 (1995), Academic Press, Inc.

* cited by examiner

*Primary Examiner*—Terry McKelvey
*Assistant Examiner*—Maria Marvich
(74) *Attorney, Agent, or Firm*—Buchanan Ingersoll PC

(57) ABSTRACT

The present invention relates to a DNA ligation method. Specifically, a DNA complex comprising a three-stranded structure in each of the ends of double-stranded DNAs, one of which has single-stranded regions at the end, and the other of which does not have single-stranded regions at the end, is formed under the presence of a homologous recombinant protein. Moreover, according to needs, the DNA complex is introduced into host cells, and said cells are cultured.

10 Claims, 13 Drawing Sheets

LIGATION OF DOUBLE-STRANDED DNAS

FIELD OF THE INVENTION

The present invention relates to gene manipulation, specifically, features a method of ligating DNA, a circular DNA constituent obtainable by said ligation method and a gene-cloning kit.

BACKGROUND OF THE INVENTION

Methods for cleaving a gene at a desired site and those for selectively ligating each gene (or DNA) are indispensable in gene manipulation. A typical example of the former is cleaving by the corresponding restriction enzyme, and further, according to needs, sequential cleaving of mononucleotides using exonucleases, provided there is a site that recognizes a restriction enzyme close to the desired site.

On the other hand, examples for the methods for ligating at a specific site are DNA ligase-mediated ligations of a cohesive end of a DNA fragment cleaved by a restriction enzyme, or a blunt-end of a DNA fragment or a blunt-end to which a suitable adapter has been added.

The method of utilizing a cohesive end cannot be applied if a restriction enzyme site corresponding to a target gene is not present, and the method of using a blunt-end requires manipulations such as isolating an objective ligate from other ligates, as the direction of ligation cannot be pinpointed.

The method of using an adapter, can be applied regardless of the type of the DNA nucleotide sequence to be ligated, however, the manipulations are complicated, requiring multistage manipulations like adapter-ligation, removal of unreacted adapters, phosphorylation, and such, and also requires some experience in these manipulations. Particularly, it is increasingly complicated when cloning just the objective gene from PCR products, as treatment of byproducts contaminating the objective PCR product becomes necessary because of the properties of PCR. The blunt-end itself that is obtained by PCR can indeed be made available for the ligation, but in this case, in addition to the need of treatments for the above-mentioned byproducts, other problems also arise, such as the direction of the ligation becoming random.

Without using restriction enzymes and DNA ligase, C. Aslanidis et al. (in Nucleic Acids Research, Vol. 18 (1990), 6069–6073) propose a method that comprises forming a bimolecular association product (circular) by a special method via single-stranded (ss) tails of a PCR product amplified using a unique repeated sequence-comprising primer, and a plasmid vector amplified in the same manner; introducing said association product into a bacteria; and selectively obtaining a circular recombinant. However, since this method requires use of a vector comprising a unique repeated sequence and a PCR primer having a corresponding sequence, and also requires single-stranding the ends of PCR products by enzymes following PCR by a special method, it cannot be said to be a versatile method.

SUMMARY OF THE INVENTION

An objective of the present invention is to provide a DNA ligation method that does not require the presence of a restriction enzyme site, is easy to manipulate, and is versatile as well.

The present inventors had a special interest in the homologous recombination of DNA in vivo. As a result of their research, it was revealed that a DNA complex formed through the Rec A protein ex vivo can be utilized in several aspects. The present invention was completed based on the findings, which are a part of the invention, that an end of the single-stranded (ss) region and an end of a double-stranded (ds) region having a homology to the said ss region end or a complementary terminal sequence, form a three-stranded region by the action of the Rec A protein, yielding a stable ligate having wide applications.

Therefore, the present invention relates to a method of ligating the ds region end of a double-stranded DNA and the ss region end of another double-stranded DNA. The method comprises contacting, under the presence of a homologous recombinant protein, the ss region end of a double-stranded DNA and the ds region end of the other double-stranded DNA which comprises a sequence that is homologous to the abovementioned ss region nucleotide sequence to form a three-stranded DNA structural complex.

Also, the present invention relates to a DNA constituent that is a circular DNA constituent provided based on the finding that a specific circular DNA capable of being formed by a ligation method such as that of the invention can exist stably under a constant ex vivo environment, and has at least a single three-stranded structural region comprised of a single-stranded region (ss region) end and a double-stranded region (ds region) end one strand of which comprises a sequence that is homologous to the nucleotide sequence of the above mentioned ss region.

Since the above-mentioned ligation method, and also means that include the formation of the above-mentioned circular DNA constituent are suitable for the cloning of desired genes, particularly PCR products, the present invention also features a kit that can be used for such clonings.

All publications, patent applications, patents, and other references mentioned herein are incorporated by reference.

BRIEF DESCRIPTION OF THE DRAWINGS

FIG. 7A shows an autoradiograph of the ethidium bromide stained agarose gel in 7B.

FIG. 8A shows an autoradiograph of the ethidium bromide stainded agarose gel in 8B.

FIG. 9A shows an autoradiograph of the ethidium bromide stained gel in FIG. 9B. In FIGS. 9A and 9B, a labeled 60mer oligonucleotide was used. FIG. 9D shows an autoradiograph of the ethidium bromide stained gel in FIG. 9C. In FIGS. 9C and 9D, a labeled 40mer oligonucleotide was used.

DETAILED DESCRIPTION OF THE INVENTION

The term "homology" used herein refers to sequence homology in a broad sense, between two types of single-stranded DNA. According to the invention, it means an identity of a sequence that is sufficient for the formation of the three-stranded structure mentioned later on. Therefore, it does not ask for a perfect tally between the nucleotide sequences of the two types of single-stranded DNAs, and preferably an identity of 95% or more will be enough. Also, the homology as defined in the present invention will be accepted even in cases where there are minor differences between the lengths of the two types of single-stranded DNA sequences. Also, being "complementary" means, when base pairs are formed mutually between the two types of single-stranded DNAs or when they are in a relationship where hybridization may occur at stringent conditions. Therefore, they should be in a relationship where at least 95% or more of both DNA sequences can form the original base pairs, and they will be accepted as being complementary, even in cases where there are minor differences between the lengths of the two types of single-stranded DNA sequences.

The present invention features a method of ligating the ss region end of a double-stranded DNA and the ds region end of another double-stranded DNA which comprises a sequence that is homologous to the nucleotide sequence of the aforementioned ss region (therefore, the other strand is complementary to said nucleotide sequence). This ligation can be presumed to occur simultaneously or sequentially at one point or at several positions in a linear DNA molecule, although ligation at two points is preferred. A circular or linear DNA ligation is formed when ligation occurs at one point or several points in each end of one or several DNAs. Although it is not restricted, the formation of a circular DNA ligate is especially preferable. DNA ligates, also named as DNA constituents or DNA recombinants in this specification, means those constructed by a single or several double-stranded DNAs.

Figure 1:
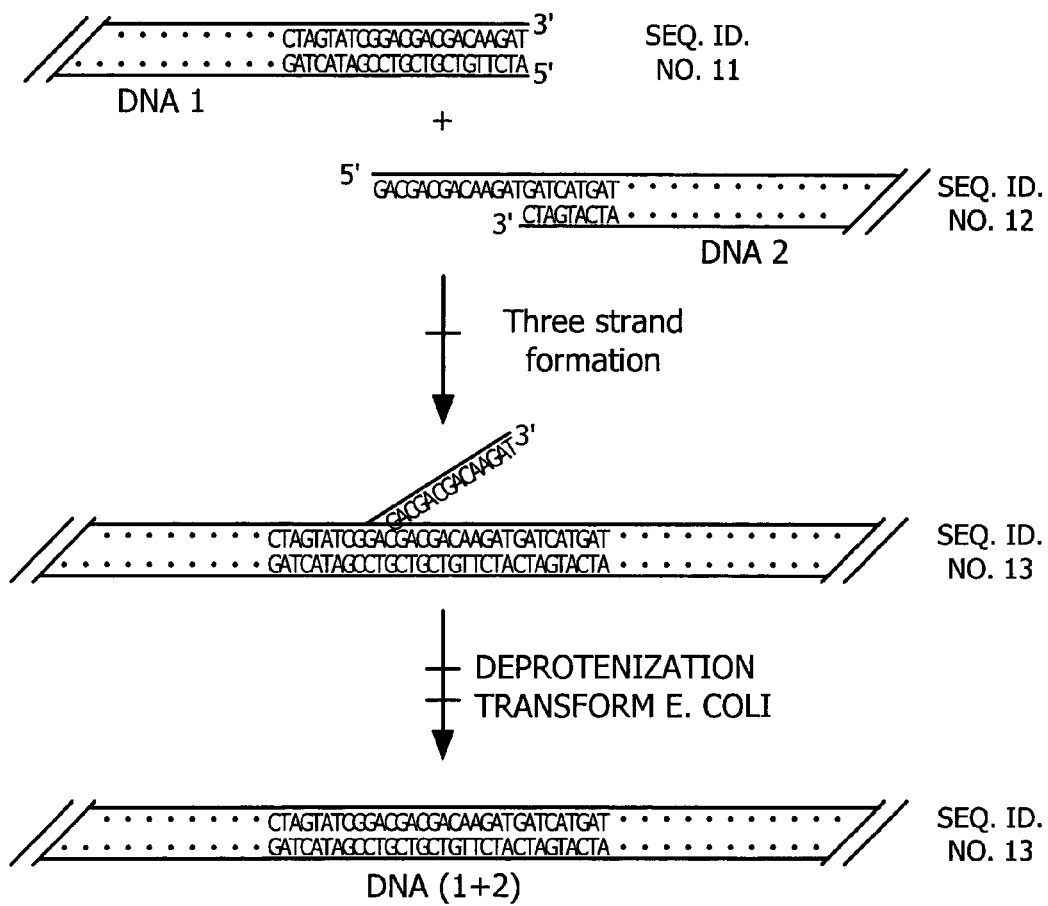
FIG. 1 shows a diagram of the reaction of the DNA cloning method by the Rec A three-strand formation reaction. DNA1 (SEQ ID NO:11) and DNA2 (SEQ ID NO:12) react according to the method of the invention to produce DNA (1+2) (SEQ ID NO:13).

The "ligation" according to the present invention, typically occurs in the manner as depicted by the simplified diagram in FIG. 1, but is not limited thereto. According to FIG. 1, although a ligation between the double-stranded region (ds region) end of DNA 1 and the single-stranded region (ss region) of DNA 2 are shown, these ds region ends and ss region ends may exist on the same DNA molecule or on two or more DNA molecules. When a ds region end and an ss region end exist on the same molecule (namely, DNA 1 and DNA 2 become one), a circular DNA constituent is formed with one three-stranded structural portion.

When the ss region end and/or ds region end exist on two or more DNAs, as shown in FIG. 1, (i) a ds region, and an ss region may each exist respectively for DNA 1 and DNA 2, or (ii) a ds region end may exist on both the 5' end and 3' end of DNA 1, and an ss region end may exist on both the 5' end and 3' end of DNA 2, or (iii) a ds region end may exist on the 5' end or the 3' end of DNA 1 and an ss region end may exist on the 3' end or the 5' end of DNA 1, and a ds region end may exist on the 5' end or the 3' end of DNA 2 and an ss region end may exist on the 3' end or the 5' end of DNA 2. The present invention also encompasses a ligation when the above DNA 1 and DNA 2 are counter-related, and when one or more additional DNA having a ds region and/or an ss region at both ends or one end are ligated.

Preferable are ligations between two kinds of DNA like those of the above-mentioned (ii) to (iii). In this case, the two ds region ends existing on DNA 1 and/or DNA 2 may have the same or different nucleotide sequences, and similarly, the two ss region ends may have the same or different nucleotide sequences corresponding respectively to the aforementioned ds region ends. "Corresponding respectively" means that a ds region end and an ss region end to be ligated, are in such a relationship that allows the formation of a three-stranded structure according to the present invention. Namely, it means that the nucleotide sequences of the sense-chain of the ds region end to be ligated, and the sense chain of the ss region end are homologous. For example, the chain corresponding to the single-stranded DNA upstream the double-stranded DNA of FIG. 1, is named in this manner (i.e., sense chain) for convenience. Also the other chain down stream is named antisense chain. As for being "homologous" refer to the prior definition.

In accordance to the present invention, the above-mentioned two ss region ends should be preferably, different nucleotide sequences, particularly those that are not mutually complementary. If such a constitution is adopted, it is possible to avoid the binding that might otherwise occur between the two ss region ends, and utilization of each ss region end for the formation of the three-stranded structure with a ds region end, will be given priority. Specially, when applying the present invention for the cloning of genes as mentioned later on, it is preferable that the two ss region ends constitute the 5' and 3' ends of the same DNA, respectively, and also, the ss region ends may exist in either the sense chain or the antisense chain, but it is preferable that an ss region end exists in each of the 3' end or 5' end of the sense-chain and the 3' end or 5' end of the antisense-chain of the same DNA.

The length of the nucleotide sequence of the aforementioned ss region ends is not restricted, and is at least 6mer, preferably 13mer or more. If it is less than 6mer, the three-stranded structure needed to accomplish the ligation according to the present invention, may lack stability. The upper limit of the above length is theoretically not restricted, and is generally 500mer (or bases) or less.

The source of the DNA applied in the method of the present invention is not questioned and may be any DNA. However, when ligating two DNAs for example, one is preferably a DNA that could be introduced into a suitable competent cell and is derived from a vector that could auto-replicate within said cells. Such vectors are selected according to the competent cells into which the ligate is introduced later on. When using *E. coli* as said cells, the commercially available, pBR322, pUC series (for example, pUC18, pSP64, pGEM-3, pBluescript) and such vectors or plasmids can be used. Also when using yeast as said cells, Yep24, Ylp5 and such, when using bacillus, pHY300, PLK and such vectors and plasmids can be used.

As for the other DNA, those derived from the genome or mitochondria of microbes or animals have been proposed, but they may also be synthesized or partially synthesized DNA, or may be derived from genetically engineered DNA.

When using the method of the invention for the cloning of genes, an embodiment into which an ss region end, which comprises a sequence that corresponds to the nucleotide sequence for both ds region ends of a DNA comprising the whole or part of the target gene, is bound to both ends of a DNA of the above-mentioned vector origin, is selected as one DNA. The aforementioned both ds region ends may be nucleotide sequences of an original gene, but also may be, for example, those that have been prepared to comprise nucleotide sequences that correspond to the whole or part of the aforementioned ss region end. An example prepared in such a manner is a PCR product made by using as the primer, an oligonucleotide comprising two ss region end sequences followed by the nucleotide sequence of the 5', or 3' end region of the target gene.

The length of the aforementioned DNA is not restricted, as long as it agrees with the objective of the invention and accomplishes the functional effects of the present invention. The appropriate scope of the aforementioned length can be understood by a person skilled in the art by referring to the whole description of the specification or the examples shown later on, or by executing experiments according to said examples.

In the present invention, the aforementioned ds region end and ss region end are contacted under the presence of a suitable homologous recombinant protein within a liquid medium. The source of such a homologous recombinant protein (or a multi-functional protein that is involved in general recombination) is not questioned, and any protein may be used, as long as the aforementioned ds region end and ss region end can form a stable complex via said protein, when the said protein is present. Specific examples of such homologous recombinant proteins are, the Rec A protein of *E. coli* origin, multi-functional proteins encoded by the Rec A gene in heat-resistant bacteria (*Thermus thermophillus*) and other enteral bacteria, and already known Rec A-like proteins of *Agrobacterium tumefaciens, Bacillus subtilis, Methylophilus methylotrophus, Vibrio cholerae, Ustilago maydis* and such origin. Yeast (*Saccharomyces cerevisiae*) and human-derived Rec-A like proteins are also encompassed in the aforementioned homologous recombinant protein. In the aspects of acquirability, stability and functioning, the *E. coli*-derived Rec A protein or a protein having a similar function is preferable for usage. For example, a modified protein of said protein origin or a fragment thereof can be used. As a modified protein, one that is a Rec A gene product created by site-specific mutagenesis of Rec A gene and such, and also comprising the amino acid sequence of the Rec A protein, in which one or more amino acids are deleted, replaced or added, and having a function equivalent to the Rec A protein, to form a complex comprising the aforementioned three-stranded DNA portion, can be given. As a modified protein, with several amino acid deletions, a peptide or protein comprising the binding-domain to single-stranded DNA of Rec A protein, can be given. Examples of such peptides are, those given in the paper of Voloshin et al., Science, Vol. 272, 1996: 868–872. As understood by the above, the word "protein" in the present invention is used as a definition that encompasses peptides as well.

At the time of the above-mentioned contact, it is preferable, or is necessary, to coexist nucleoside triphosphates (dATP, dUTP, dCTP, dTTP, cGTP, ATP, TTP, CTP, UTP, GTP). Examples of such nucleoside triphosphates are, adenosine 5'-triphosphate (ATP) or its analog, for example, adenosine (γ-thio)-triphosphate (ATP-γS), GDP-γS, AMP-PNP, or regenerating systems (NTP+Phosphocreatine+creatine phosphokinease) of NTP (ATP, TTP, GTP, CTP). In the above complex-formation system, when ATP handles the biological degradation, it is preferable to use ATP-γS.

The above contact is done in a suitable liquid medium, for example, in solutions that are safe to be buffered by suitable buffer agents. For example, a Tris-type buffer prepared by adjusting the pH to 6.5 to 7.5, preferably, about 7.2 with Tris (namely, Tris (hydroxymethyl) aminomethane) and a suitable acid (for example, acetic acid, hydrochloric acid). The buffer agent is generally used at 10 mM to 50 mM, preferably about 30 mM. The aforementioned DNA to be ligated is dissolved in such a liquid medium, the homologous recombinant protein and nucleoside triphosphate are added, and the mixed solution is incubated to execute the above-mentioned contact.

The ratio of DNAs to be ligated is not restricted, and may be any, as long as they are within a range that does not adversely affect the correct ligation of each end. However, when using the method of the invention for cloning of a specific gene, it is preferable to use the DNA to be ligated in a concentration that is almost equimolar to the DNA comprising the whole or partial gene. The ratio of the homologous recombinant protein used cannot be restricted as it varies according to the ss region chain-length, but is generally a molar amount that exceeds the nucleotide number constituting the ss region, and is preferably, about one molar amount against three nucleotides.

The "contact" according to the present invention can be completed by incubating the mixture prepared as mentioned above at 4 to 54, preferably for 15 min at about 37, generally for 30 min. As a result, a DNA ligate (or DNA constituent) comprising at least one three-stranded structural portion is formed.

The DNA constituent thus formed, generally exists in the form of a complex into which at least the homologous recombinant protein is bound to the three-strand structural portion. Such complexes, can be isolated from the reaction-mixture by suitable purification methods, for example, by phenol-chloroform extraction, gel filtration and various electrophoresis methods. The complex thus isolated is stable at normal, exogenous physiological conditions and can be used for analysis of genes and DNA sequences constituting the complex.

Without isolating the above complex from the reaction-mixture (or sometimes after isolating), the homologous recombinant protein can be removed from the complex by treating with proteinases (for example, proteinase R). The DNA constituent thus deproteinized, is also stable. That which is formed by the ligation of two types of DNA and has a three-stranded structure at two sites, is especially stable, and further can be efficiently introduced into cells by ordinary methods in the art. Prior to the introduction, conversion of the three-stranded structural portion (refer to FIG. 1) to a double-stranded structure by an endonuclease that specifically acts on a single-stranded nucleic acid, enables the DNA constituent to be more efficiently introduced into a cell.

The method of introduction can be suitably selected according to the starting material (vector) of the vector-derived DNA used as one of the DNAs. For example, when selecting an vector capable of auto-replicating inside *E. coli* as a vector or plasmid, and *E. coli* as the competent cell, introduction of the DNA constituent can be done using method such as electroporation method and calcium-treatment method. By culturing cells into which the above DNA constituent has been introduced, a circular DNA constituent can be amplified, in which the above-mentioned three-stranded structural region (when present) had been converted to double-stranded structural region. This structural region is presumed to be in a state in which the nucleotide sequence corresponding to the above-mentioned ss region end has been removed from the abovementioned ds region end, and in which the ds region end and the ss region end is covalently-linked via a phosphodiester bond.

If ordinary methods used to introduce a gene into the aforementioned cells are followed, a circular DNA constituent will be more efficiently introduced into a cell than a linear DNA constituent. Therefore, when applying the method of the present invention using a PCR product as the DNA having the ds region end, those byproducts that are not correctly elongated by PCR will not be introduced to cells, since they do not form circular DNA constituents. The above-mentioned PCR product is obtained by a PCR reaction that uses as a primer, an oligonucleotide comprising nucleotide sequences corresponding respectively to the two types of ss region ends followed by each of the nucleotide sequences of the 5 or 3 end region of the gene to be ligated, and uses said gene as a template. Therefore, only the PCR products resulting from the correct amplification of the gene to be cloned by PCR, can be obtained by the method of the present invention.

Since the above circular DNA constituent can auto-replicate within a suitable cell, the circular DNA constituent as-it-is or its replicate can be utilized for the analysis of the DNA sequence or structure or function of the gene contained in the circular DNA constituent. Therefore, another embodiment of the invention provides a DNA constituent that is a circular DNA and has at least one three-stranded structural region made from a single-stranded region (ss region) end and a double-stranded region (ds region) end comprising a sequence that is homologous to the abovementioned ss region end. Such a DNA constituent is made from the aforementioned two DNAs, one of them having a nucleotide sequence that is capable of auto-replicating within a cell, and the other comprising the whole or part of the gene to be cloned, and preferably having in addition, two three-stranded structural regions. The size of "the part of the gene" is not questioned, as long as it has a nucleotide sequence sufficient to distinguish it from other genes. Furthermore, two or more genes may be comprised.

Examples of methods for converting a three-stranded structure to a double-stranded structure are, (1) the method that comprises transfecting the nucleic acid ligate obtained by the three-strand formation reaction into a prokaryotic or eukaryotic cell, and converting the nucleic acid-ligated region including the three-strand structure into double-stranded DNA, or (2) the method of converting the nucleic acid-ligated region including the three-strand structure into double-stranded DNA using nucleic-acid modification enzymes, within a test tube.

The following two representative gene transfection methods can be given as methods for converting the nucleic acid-ligated region including the three-strand structure into double-stranded DNA within prokaryotic/eukaryotic cells into which the nucleic acid ligate obtained by the three-strand formation reaction has been introduced.

Using chemical gene-transduction methods, the nucleic acid ligate that has been subjected to the three-strand formation, is introduced into colibacili (*Escherichia coli*), fission yeasts (*Saccharomyces cerevisiae*), budding yeasts (*S. Pombe*), *Pichia* (*Pichia pastoris*) and such prokaryotic or eukaryotic competent cells, and the nucleic acid structure formed by the ligation reaction, including the three-strand formation region that is the DNA binding site, can be converted into the original double-stranded structure within the competent cells.

Alternatively, using the electroporation method, the nucleic acid ligate that has been subjected to the three-strand formation can be introduced to mammalian culture cells such as human hybridoma, plant protoplasts typified by tobacco protoplasts, plants typified by corn, microbial cells typified by fission yeasts (*Saccharomyces cerevisiae*), or bacteria typified by *E. coli* and *lactobacillus*, and the nucleic acid structure formed by the ligation reaction, including the three-strand formation region that is the DNA binding site, can be converted into the original double-stranded structure within the above cells.

As a method of converting the nucleic acid-ligated region including the three-stranded structure into double-stranded DNA using nucleic-acid modification enzymes, within a test tube, for example, the two representative modification enzymes shown next can be used alone or in combination to convert the nucleic acid ligation region including the three-strand formation into a complete double-stranded DNA or, a double-stranded DNA that is incomplete with nicks and such still remaining.

The nucleic acid structure formed by the ligation reaction, including the three-strand formation region that is the DNA binding site, can also be converted into the original double-stranded structure, by using a Klenow fragment through its polymerase activity and the 3'→5', exonuclease activity. Also, in the nucleic acid ligate that has been subjected to the three-strand formation, the structure of the three-strand formation that is the DNA ligation site, can be converted into the original double-stranded DNA.

As mentioned above, the method of the present invention can be applied for cloning of genes. Such a cloning can be implemented conveniently by the gene-cloning kit described below, which is provided as a different embodiment. Such a kit comprises at least;

(A) a double-stranded DNA comprising a single-strand region (ss region) at both ends, in which the nucleotide sequences at these ss regions are mutually non-complementary, and is also a DNA sequence that can provide the double-stranded region the capacity to auto-proliferate within competent cells.

(B) an oligonucleotide primer having, as a part of the 5' end sequence, a sequence that is homologous to the nucleotide sequence of the above mentioned one ss region, and further comprising a part of the sequence of the other end in the gene to be cloned, and, (C) an oligonucleotide primer having, as a part of the 5' end sequence, a sequence homologous to the nucleotide sequence of the above mentioned other ss region, and further comprising a part of the sequence of the end other than that in (B), in the gene to be cloned.

The lengths of the aforementioned ss region nucleotide sequence and the double-stranded-region (namely, derived from the vector or plasmid that is capable of auto-replicating within competent cells), are as already mentioned. Also, lengths of the partial sequence of one end of the gene to be cloned and that of the partial sequence of the other end, are lengths that function as primers of PCR, when each of them combine with the above mentioned ss region, when the said gene is used as the template.

According to one embodiment of the usage of the kit of the present invention, ligation is carried-out between the DNA of (A), and PCR products (corresponds to the DNA comprising a ds region end) amplified by using the primers of (B) and (C). As stated above, the ligation is done under the presence of a homologous recombinant protein and nucleoside triphosphate within a suitably buffered aqueous solution. Therefore, other than the above DNA samples, the kit of the invention may contain an above-mentioned protein, nucleoside triphosphate and a buffering agent. Moreover, it may also include a proteinase for the removal of an above-mentioned protein that is bound to the DNA constituent obtained by ligation.

The ligation method of the invention has the following characteristics.

(i) Ligation is possible even when there are no suitable restriction enzyme sites on the DNA to be ligated.

(ii) It is possible to avoid contamination of byproducts, which is undesirable in gene cloning, as the auto-ligation reaction of vector DNA does not occur since no ligation enzymes are used.

(iii) Since the ligation-site will be usually repaired within competent cells into which the ligate is introduced as the next step, a ligation is not necessarily needed.

(iv) When applying for cloning of PCR products, though not restricted thereto, the background is low as PCR byproducts are not introduced into competent cells.

(v) Nucleotide-specificity and orientation-specificity can be conferred to the ligation since a homologous recombinant protein (i.e. Rec A) is used.

(vi) Transformation can be done according to conventional methods, with an equal or higher efficiency.

(vii) Versatility is higher than the above-mentioned method of C. Aslandis et al. since no special vectors are needed.

Therefore, the present invention is highly useful in the technical field pertaining to gene-manipulation.

Figure 2:
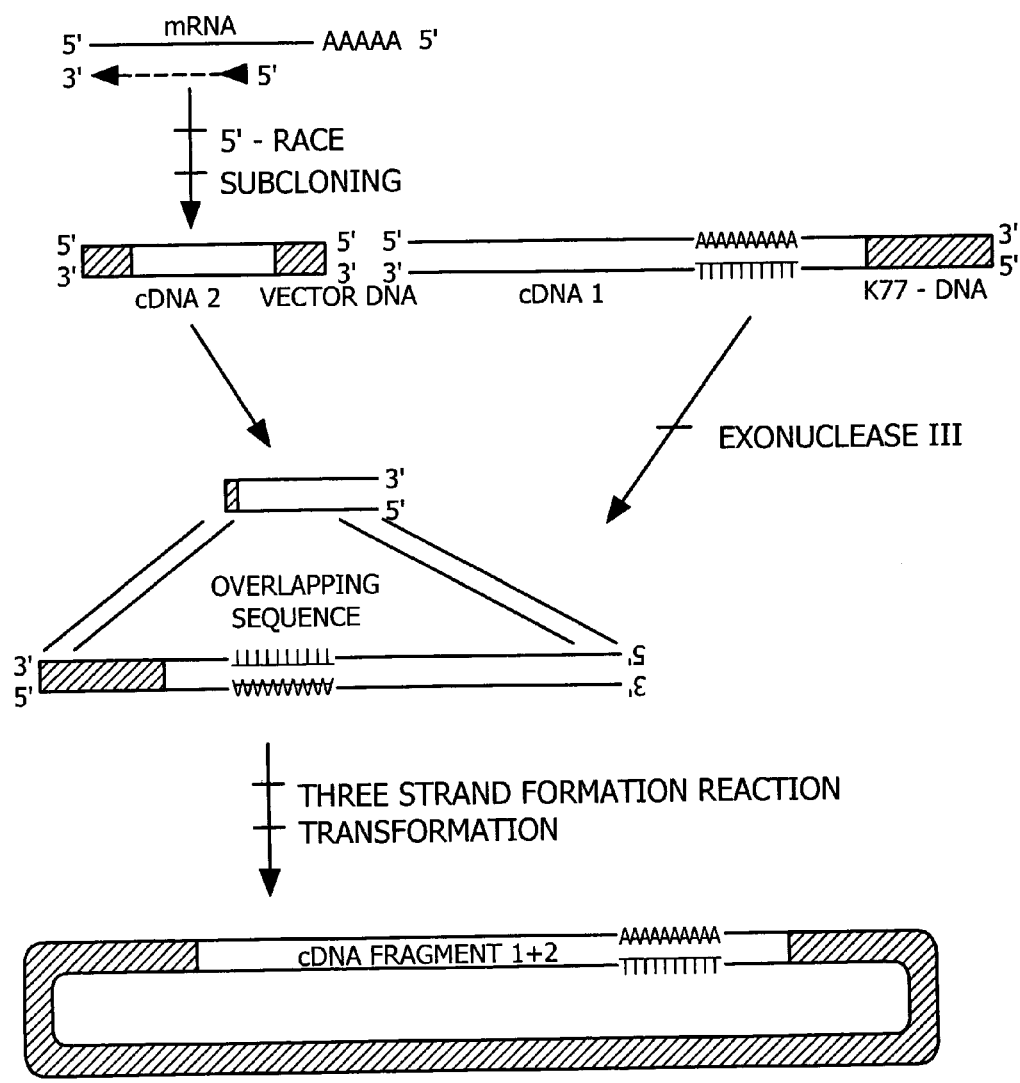
FIG. 2 shows a diagram of the 5'RACE reaction by the Rec A three-strand formation reaction. cDNA1 and cDNA 2 react according to the method of the invention to produce cDNA fragment 1+2. cDNA1 contains a small stretch of 10 polyA nucleotides (SEQ ID NO:14)

The present invention displays a dramatic effect for 5' RACE (A. Michael et al., Proc. Natl. Acad. Sci USA, Vol. 85 (1998), 8998–9002) (refer to FIG. 2). For example, the following reaction can be executed. In FIG. 2, cDNA1 corresponding to the 3' end side sequence of cDNA overlaps at some parts, with cDNA2, which corresponds to the sequence more to the 5' end side than cDNA1, which was amplified using the 5' side sequence of cDNA1 as the primer and cDNA as the template. This overlapping double-stranded region is converted into a single-stranded region by reacting exonuclease III on cDNA1, the double-stranded DNA (cDNA2) and single-stranded DNA (cDNA1) in this overlapping portion are then formed into a three-stranded structure by the method of the invention, and then transformed to make a double-stranded DNA. By this manipulation, cDNA1 and cDNA2 can be obtained as a sequential cDNA sequence without any gaps.

The present invention will be described in detail below, with reference to examples, but is not to be construed being limited thereto.

EXAMPLE 1

DNA Cloning Using the Rec A Protein

Figure 3:
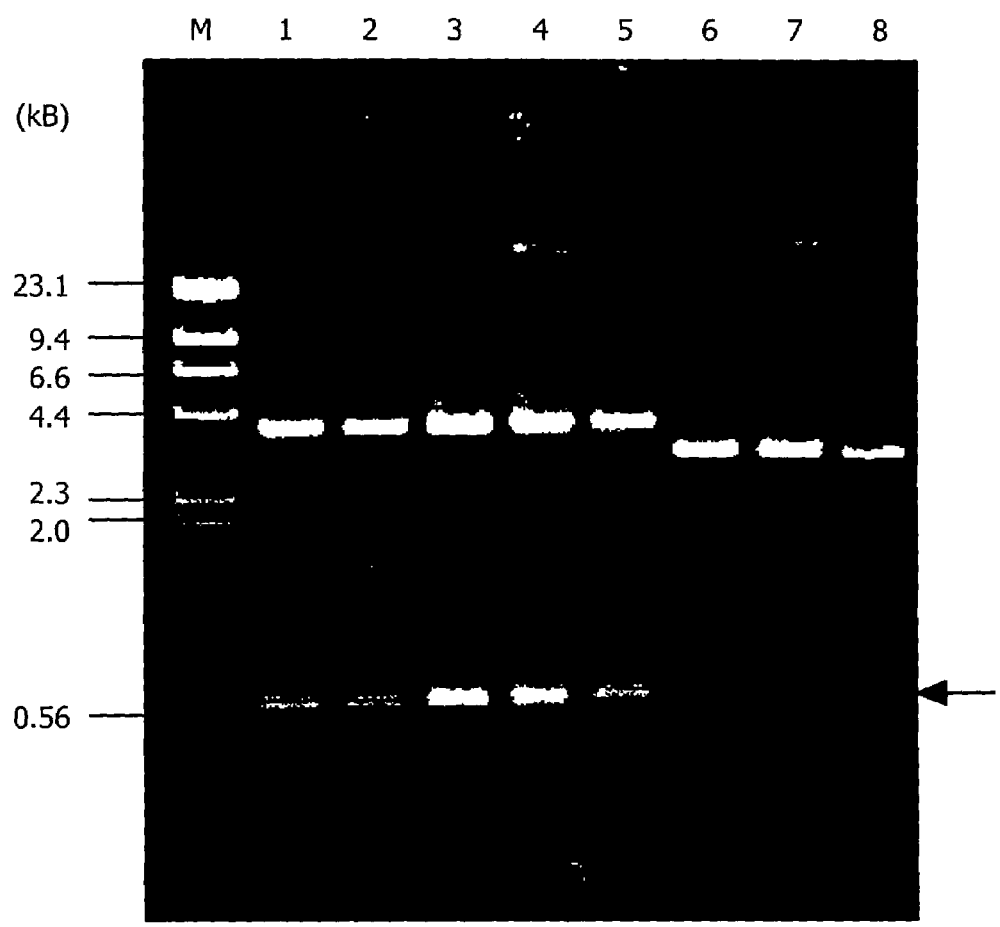
FIG. 3 shows a photograph of the gel electrophoretic pattern obtained in Example 1, in which the DNA cloning by the Rec A three-strand formation reaction was done.

A linear vector DNA, both sides of which have 3' protruding ends of 13 mer (sequence A) and 14mer (sequence B), was prepared as the vector DNA. The amplification products obtained by a PCR done using oligonucleotide 1 comprising sequence A at the 5' end followed by the sequence of one end of exon 11 of human p53 gene, oligonucleotide 2 comprising sequence B at the 5'end followed by the other end sequence of exon 11, and human genomic DNA as the template, was prepared as the insert DNA. Three-strand formation reaction was done between the aforementioned vector DNA and insert DNA. In 40 μl of the reaction solution, 200 ng insert DNA, 6.0% g Rec A protein, 4.8 mM ATP-γS, 30 mM Tris-acetate (pH7.2), 1 μg vector DNA, and 21.5 mM magnesium acetate are contained. This reaction solution was incubated at 37° C. for 30 min. 0.5% (W/Vol) SDS, and 0.7 mg/ml proteinase K were added, incubated at 37° C. for 30 min, and then 60 μl TE Buffer (10 mM Tris-HCl, 1 mM EDTA) was added to make a total volume of 100 μl. After doing a single phenol-chloroform extraction, and a single chloroform extraction, ethanol precipitation was done, and DNA was dissolved in 10 μl distilled water. 2 ml thereof was transformed into *E. coli* cell line DH10B by the usual electrophoresis. After culturing overnight in an agar medium containing ampicillin, IPTG, and X-Gal, plasmids were prepared from the resulting white-colonies containing inserts, and the insert DNA was then examined. The presence of the site recognized by the restriction enzyme BamH1 in around the center of the insert DNA and close to the site into which the DNA insert is integrated in the vector DNA, was verified. Next, when the insert DNA was excised using BamH1, the electrophoretic pattern of the DNA was simultaneously analyzed by agarose gel electrophoresis in order to verify whether the insert DNA is the targeted one or not. The result is shown in FIG. 3. Lane 1 to Lane 5 in this figure shows the derivatives of plasmids prepared from the white colonies resulting from the culture, lane 6 to lane 7 are derivatives of plasmids prepared from the blue colonies resulting from the culture. Lane M shows the DNA size markers, and the sizes are shown on left edge of the figure. These size markers were those obtained by cleaving λDNA by the restriction enzyme HindIII.

From this figure, the excised DNA band is visible at the position around 600 bp. It was also verified that a part of the insert DNA has ligated in the intended orientation in the vector DNA. Also, it is perceived that the insert non-comprising blue colony plasmids do not contain the insert.

Oligonucleotide 1 (SEQ ID NO: 1)
5'-gacgacgacaaga c acctgaagtc caaaaagggt cagtc-3'
Oligonucleotide 2 (SEQ ID No: 2)
5'-gaggagaagcccgg tggcag caaagttta ttgtaaaata-3'

(In the above sequence, the sequences from the $14^{th}$ c and beyond, and from the $15^{th}$ t and beyond, correspond to the human genomic sequence).

EXAMPLE 2

Verification of the Ligated DNA

Figure 4:
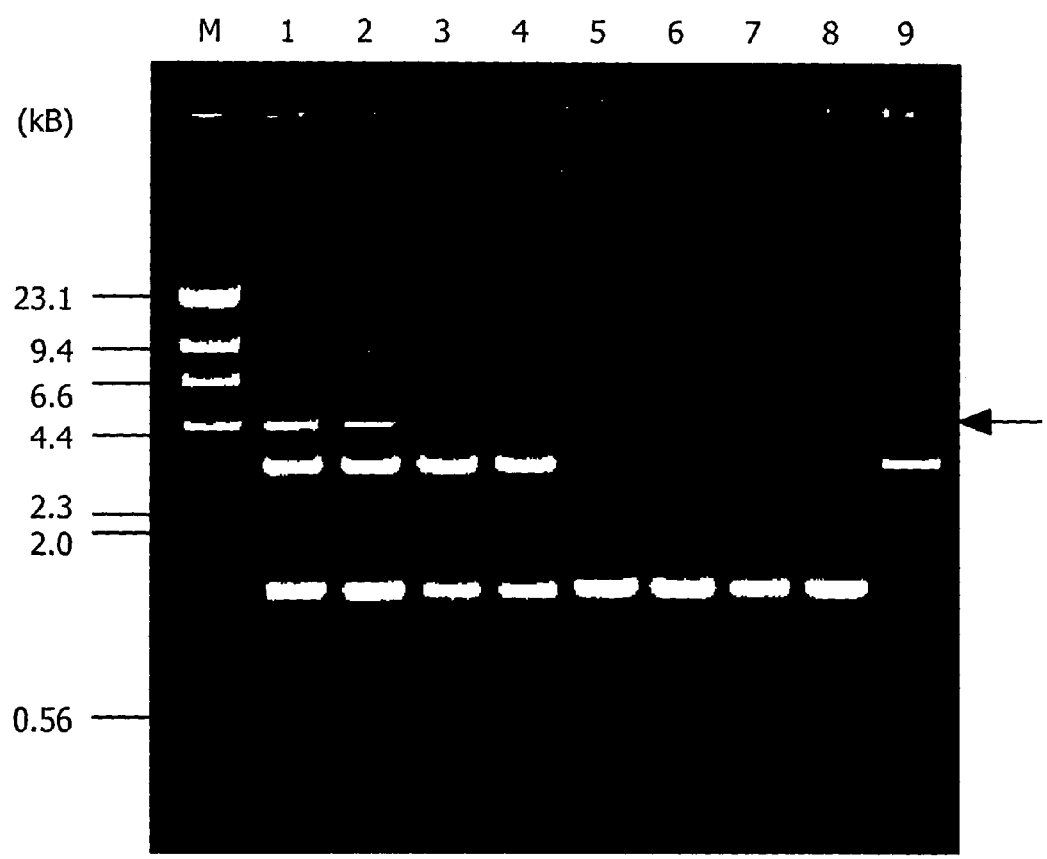
FIG. 4 shows a photograph of the gel electrophoretic pattern obtained in Example 2, in which the DNA ligated by the Rec A three-strand formation reaction was confirmed.

Lane 1 of FIG. 4 is the result of 10% agarose gel electrophoresis of the DNA mixture before transforming into E. coli in Example 1. Lane 2 is the result of a similar electrophoresis of the DNA mixture before transforming into E. coli, and the DNA mixture was obtained by the reaction using the insert DNA of Example 1 comprising sequence A but not sequence B at both ends. Lane 3 is the result of a similar electrophoresis of the DNA mixture before transforming into E. Coli, the DNA mixture obtained by the reaction using the insert DNA of Example 1 comprising sequence B but not sequence A at both ends. Lane 4 is the result of a similar electrophoresis of the DNA mixture before transforming into E. coli, the DNA mixture obtained by the reaction using the insert DNA of Example 1 comprising neither sequence A nor sequence B in the respective ends (oligonucleotide 3 and 4, respectively). Lane 5 is the result of an electrophoresis of only the insert DNA used in lane 1. Lane 6 is the result of an electrophoresis of only the insert DNA used in lane 2. Lane 7 is the result of an electrophoresis of only the insert DNA used in lane 3. Lane 8 is the result of an electrophoresis of only the insert DNA used in lane 4. Lane 9 is the vector DNA used. Lane M shows the size markers, and the sizes are given on the left edge of the figure. These size markers were those obtained by cleaving λDNA by the restriction enzyme HindIII.

From this figure, it was revealed that DNA is ligated in a sequence-specific manner by the Rec A reaction.
Oligonucleotide 3 (SEQ ID NO:3)
5'-c acctgaagtc caaaagggt cagtc-31
Oligonucleotide 3 (SEQ ID NO:4)
5'-tggcag caaagtttta ttgtaaaata-31

The same sample as in lanes 1 to 4 of FIG. 4, and lane 9, was transformed into E. coli cell line DH10B by the usual method of electroporation. Then after an overnight culture in agar medium containing ampicillin, IPTG, and X-Gal, the number of resulting E. coli colonies were counted. The result is shown in Table 1.

TABLE 1

| | Lane number | | | | |
|---|---|---|---|---|---|
| | 1 | 2 | 3 | 4 | 9 |
| White colony number | 183 | 0 | 0 | 0 | 0 |
| Blue colony number | 243 | 220 | 288 | 73 | 133 |

(Note that "white colony" in Table 1 refers to a colony comprising insert DNA that has been inserted into the vector, and "blue colony" refers to a colony that does not harbor the insert DNA).

As seen from Table 1 and Figure, DNA is ligated in a sequence-specific manner by the Rec A reaction.

EXAMPLE 3

The Enzyme-Dependency of the Ligation Reaction

Figure 5:
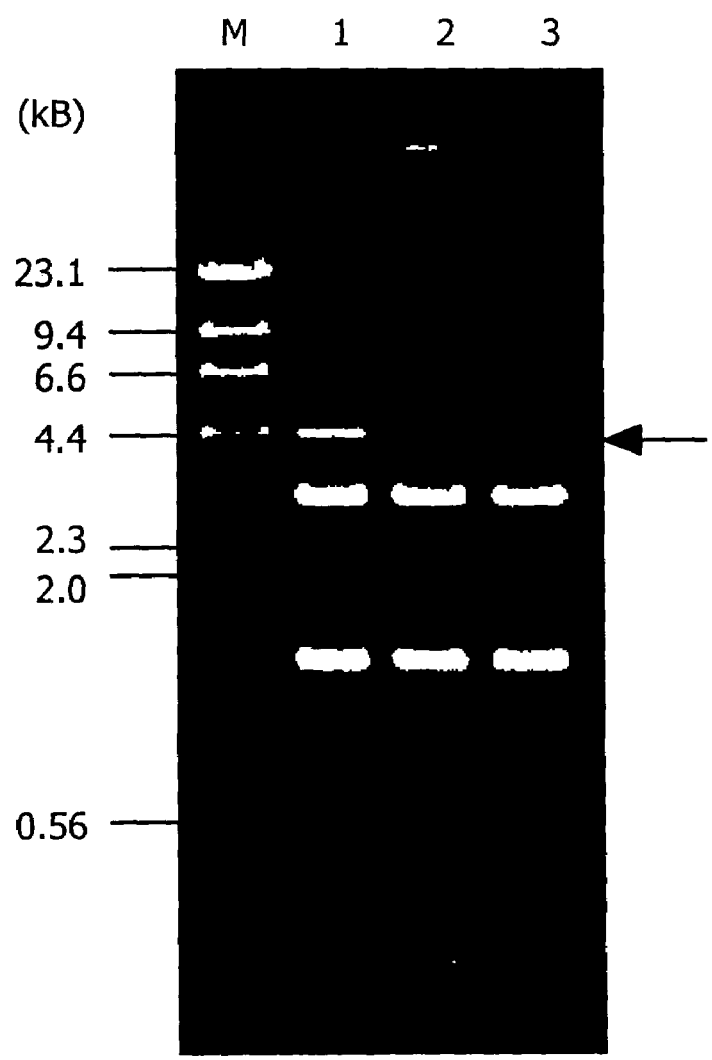
FIG. 5 shows a photograph of the gel electrophoretic pattern obtained in Example 3, in which the enzyme dependency of the ligation reaction of the DNA ligated by the Rec A three-strand formation was examined.

Lane 1 of FIG. 5 shows the result of 10% agarose gel electrophoresis of the DNA mixture used for the transformation into E. coli in Example 1. Lane 2 shows results of the same reaction without adding ATP-γS. Lane 3 shows results of the same reaction without adding Rec A. Lane M shows the size markers, and the sizes are given on the left edge of the figure. These size markers were those obtained by cleaving λDNA by the restriction enzyme HindIII.

From the figure, it is revealed that the enzyme reaction is absolutely necessary for Rec A mediated ligation of target DNA.

EXAMPLE 4

The Stability of Ligated DNA

Figure 6:
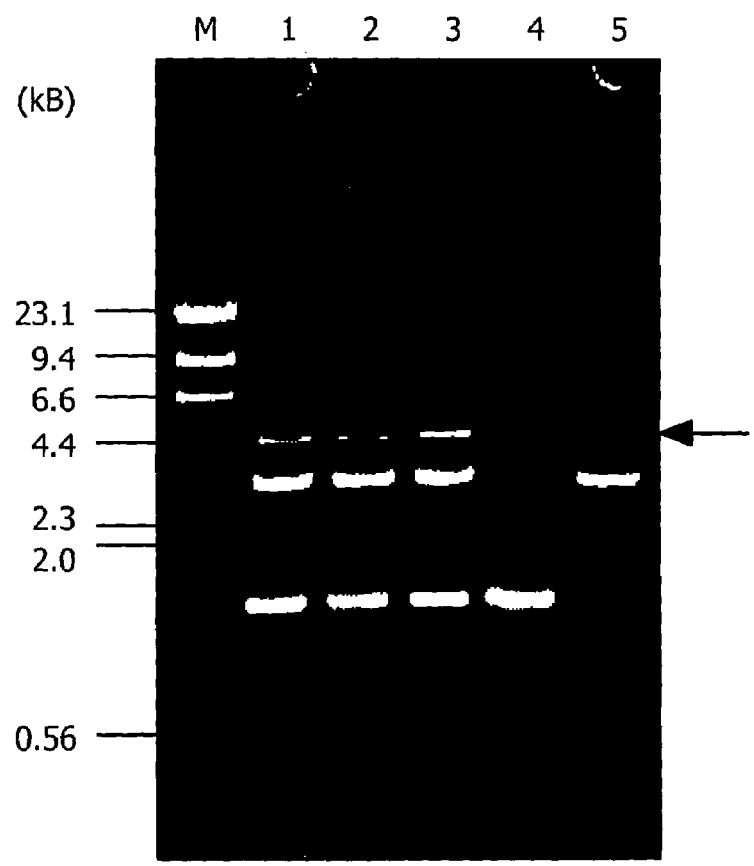
FIG. 6 shows a photograph of the gel electrophoretic pattern obtained in Example 4, in which the heat-stability of the ligated DNA ligated by the Rec A three-strand formation was examined.

The stability of ligated DNA was examined via the formation of the three-stranded structure. It was examined whether it is possible to treat the ligated DNA with various modification enzymes prior to the transformation into E. coli, according to needs. Heat-stable DNA ligase (Ampligase), which is one of the modification enzymes, was tested herein. Specifically the reaction is as follows. In the reaction of Example 1, after incubating at 37° C. for 30 min, an equivalent amount of the ligation reaction solution was added thereto, mixed, and incubated at 55° C. for 1 hour. The ligation reaction solution contained 40 mM Tris-HCl, 50 mM KCl, 20 mM $MgCl_2$, 1.0 mM NAD, 0.02% Triton X-100, pH8.3, and 40 units Ampligase. Next, 0.5% (W/Vol) SDS, and 0.7 mg/ml proteinase K were added, was incubated at 37° C. for 10 min, and then 20 ml TE Buffer solution (10 mM Tris-HCl, 1 mM EDTA) was added to make a total volume of 100%1. The DNA molecules contained were concentrated and isolated with a single phenol-chloroform extraction and a single chloroform extraction, followed by ethanol precipitation. The resulting DNA was dissolved in 10 µl distilled water. 1.0% Agarose gel electrophoresis was carried-out for the whole amount. After electrophoresis, ethidium bromide staining was done, and photographs taken to observe DNA. Lane 1 of FIG. 6, shows the results. Lane 2 shows the result for the same reaction as in lane 1, without adding Ampligase. Lane 3 shows the results for the same reaction as in lane 1 when distilled water was used in place of above reaction solution and when the incubation of the ligation was not done. Lane M shows the size markers, and the sizes are given on the left edge of the figure. These size markers were those obtained by cleaving λDNA by the restriction enzyme HindIII.

FIG. 6 shows that there was no considerable change in the electrophoretic pattern, even after the ligated DNA was incubated for 1 hour at 55° C. in Ampligase buffer solution. The results of lane 2 and lane 3 show that the DNA complex formed by the present invention is extremely stable. Hence, it is possible to carry out ligation by DNA ligase under the presence of the Rec A protein, if necessary. It is possible to integrate insert DNA into vector DNA by a covalent bond, and also, to modify nicks in DNA. And also, modifications of various ligated DNA complexes are possible using other heat-resistant DNA modification enzymes.

EXAMPLE 5

The Dependency of Each Reactant in the Three-Strand Formation Reaction

As the target DNA, M13mp18RF DNA linearized by the restriction enzyme SnaBI, and 60mer oligonucleotide 5 comprising the sequence of the target DNA end region were prepared. The 5' end of this oligonucleotide was labeled with $^{32}P$ using [γ-$^{32}P$] ATP. For the three-strand formation reaction between target DNA and oligonucleotide 5, 1 pmol of labeled oligonucleotide, 6.0 µg of Rec A protein, 4.8 mM ATP-γs 30 mM Tris-acetate (pH7.2), 200 ng of target DNA, and 21.5 mM magnesium acetate were contained in 40 ml of reaction solution. After adding 0.5% (W/Vol) SDS, and 0.7 mg/ml proteinase K, the reaction solution was incubated at 37° C. for 30 min to remove Rec A. Then the whole amount was subjected to 1% agarose gel electrophoresis after which ethidium bromide staining was done and photographs of the gel are taken. The result is shown in FIG. 7 (B). The gel was then placed on top of a filter paper and dried in a drier. The detection of the signal was recorded on an X-ray film, by an autoradiography of the dried gel. FIG. 7 (A) lane 1 shows the result. What follows is the comparative experiment. Lane M shows the size markers and the sizes are given on the left edge of the figure. These size markers were obtained by cleaving λDNA with restriction enzyme HindIII, and the 5' ends were labeled with $^{32}$P using [γ-$^{32}$P] ATP. Lane 2 is equivalent to lane 1, expect for the fact that the reaction was done without Rec A. Lane 3 is equivalent to lane 1, expect for the fact that the reaction was done without ATP-γS. Lane 4 is equivalent to lane 1, expect for the fact that the reaction was done with reverse complementary oligonucleotide 6. Lane 5 is equivalent to lane 1, expect for the fact that the reaction was done without an oligonucleotide. Lane 6 is equivalent to lane 1, expect for the fact that the reaction was done with oligonucleotide 7. In Lane 7 is the sample for which the reaction was done using oligonucleotide 7 against the target DNA obtained by cleaving pBR322 DNA with restriction enzyme ScaI. Lane 7 is equivalent to lane 1, expect for the fact that pBR322 DNA cleaved by restriction enzyme Sca I was used as the target DNA, and also the fact that labeled oligonucleotide 7 having the end region sequence of the said target DNA was used.

From the figure and as shown in lane 1 of (A), the three-strand formation requires the addition of all the reactants to the reaction. Also, since the three-strand formation cannot be obtained with a reverse complementary oligonucleotide and a reverse homologous nucleotide, the orientation of the oligonucleotide is unidirectional.

Oligonucleotide 5 (SEQ ID NO: 5)
5'-agaggctttg aggactaaag acttttcat gaggaagttt ccattaaacg ggtaaaatac-3'
Oligonucleotide 6 (SEQ ID NO: 6)
5'-gtattttacc cgtttaatgg aaacttcctc atgaaaagt ctttagtcct caaagcctct-3'
Oligonucleotide 7 (SEQ ID NO: 7)
5'-cact gcataattct cttactgtca tgccatccgt aagatgcttt tctgtgactg gtgagt-3'

EXAMPLE 6

Figure 7A:
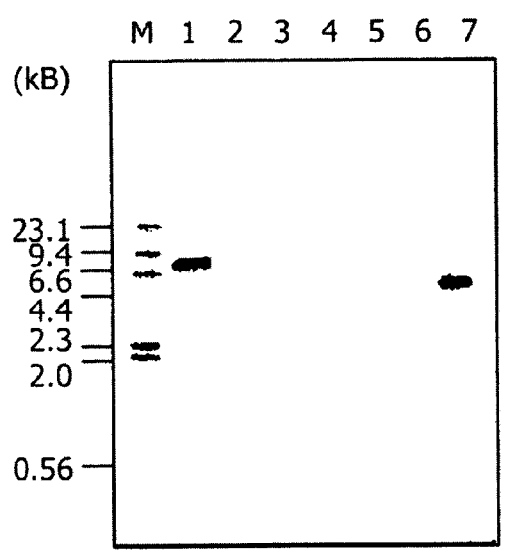
FIGS. 7A and 7B show photographs of the gel electrophoretic pattern obtained in Example 5, in which the dependency of each reactant in the DNA end three-strand formation reaction using oligonucleotides was examined.
Figure 7B:
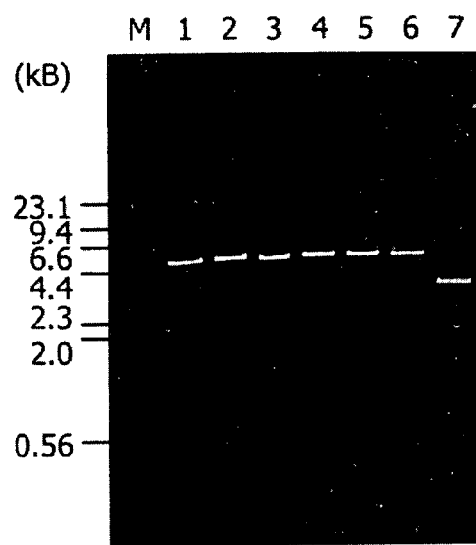
Figure 8A:
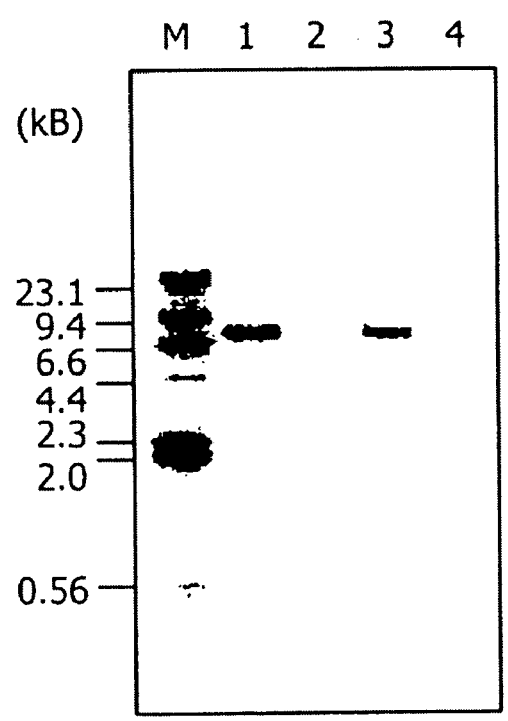
FIGS. 8A and 8B show photographs of the gel electrophoretic pattern obtained in Example 6, in which the sequence-orientation of oligonucleotides in the DNA end three-strand formation reaction using oligonucleotides, was examined.
Figure 8B:
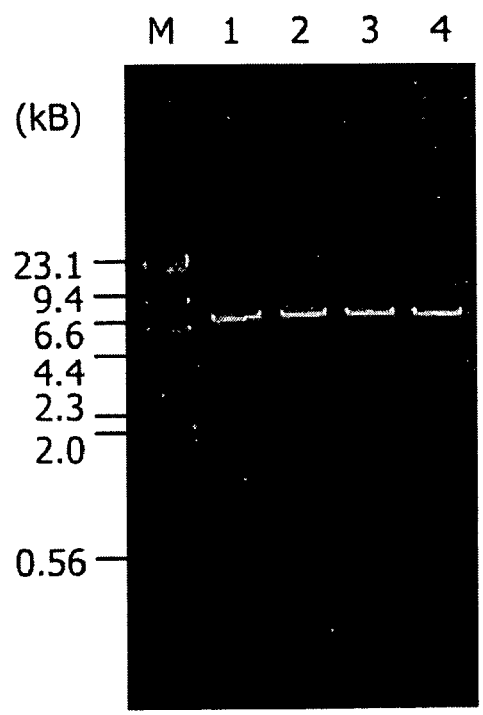
Figure 9A:
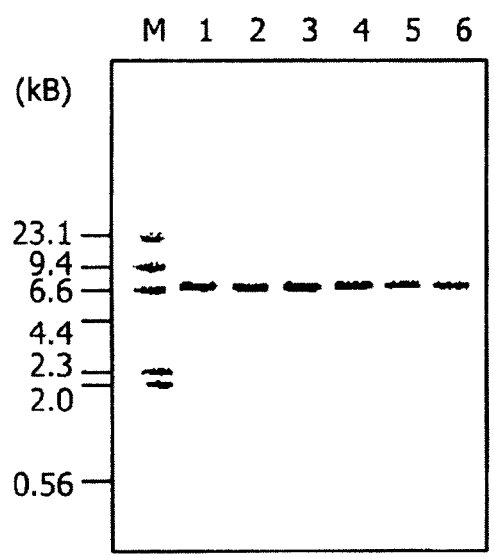
FIGS. 9A–9D show a photograph of the gel electrophoretic pattern obtained in Example 7, in which the heat stability of oligonucleotide sequence in the DNA end three-strand formation reaction, was examined.
Figure 9B:
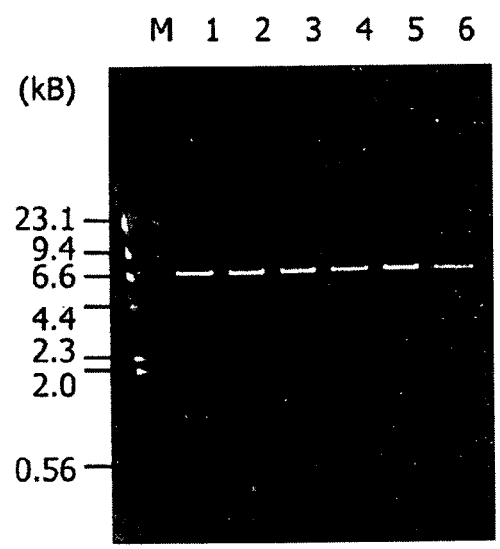
Figure 9C:
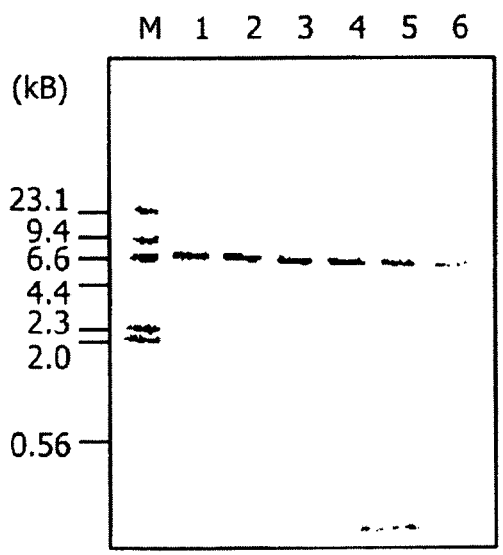
Figure 9D:
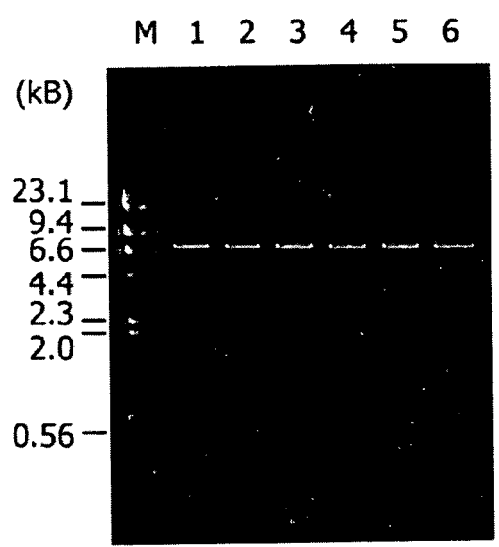

Sequence Orientation of the Nucleotides Used in the Three-Strand Formation Reaction The same reaction as in lane 1 of FIG. 7(A) was carried out in FIG. 8 (A), lane 1. Lane 2 is the same reaction as lane 1, except for the fact that labeled oligonucleotide 4 comprising a reverse complimentary sequence was used. Lane 3 is the same reaction as lane 1, except for the fact that labeled oligonucleotide 8 was used. Lane 4 is the same reaction as lane 1, except for the fact that a labeled oligonucleotide 9 was used. (B) shows photograph of a whole DNA staining of the same agarose gel as in (A).

The figure shows that three-strand formation at both ends of the linear target DNA is possible and that oligonucleotides used at that instance should be homologous sequences with the same direction of one of both end sequences of the target. Oligonucleotide 8 (SEQ ID NO: 8)

5'-tgttttagtg tattctttcg cctctttcgt tttaggttgg tgccttcgta gtggcattac-3'
Oligonucleotide 9 (SEQ ID NO: 9)
5'-gtaatgccac tacgaaggca ccaacctaaa acgaaagagg cgaaagaata cactaaaaca-3'

EXAMPLE 7

Heat-Stability of the Oligonucleotide Sequences for the Three-Stranded Structure Formation Lane 1 of FIG. 9 (A) shows the sample to which the same reaction as in FIG. 8 (A) lane 1 was first done, followed by the addition of 20 mM NaCl to 10 µl of the sample and heat-treatment for 10 min at 37° C. Lane 2 has the sample to which heat-treatment was done for 10 min at 45° C. Lane 3 has the sample to which heat-treatment was done for 10 min at 55° C. Lane 4 has the sample to which heat-treatment was done for 10 min at 65° C. Lane 5 has the sample to which heat-treatment was done for 10 min at 75° C. Lane 6 has the sample to which heat-treatment was done for 10 min at 85° C. (B) shows photograph of a whole DNA staining of the same agarose gel as in (A). In (C), the same experiment as in (A) was done using 40mer-long oligonucleotide 10 comprising the sequence of the target DNA (M13 mp18RF DNA cleaved by restriction enzyme SnaBI) end region. (D) shows photograph of a whole DNA staining of the same agarose gel as in (C).

Oligonucleotide 10 (SEQ ID NO: 10)
5'-acttttcat gaggaagttt ccattaaacg ggtaaaatac-3'

Figure shows that a temperature around 85° C. is roughly the limit of the heat-stability of the three strand using oligonucleotide 5 of 60mer, and it is around 75° C. when using oligonucleotide 10 of 40mer.

EXAMPLE 8 cDNA Cloning by Rec A Reaction

Figure 10:
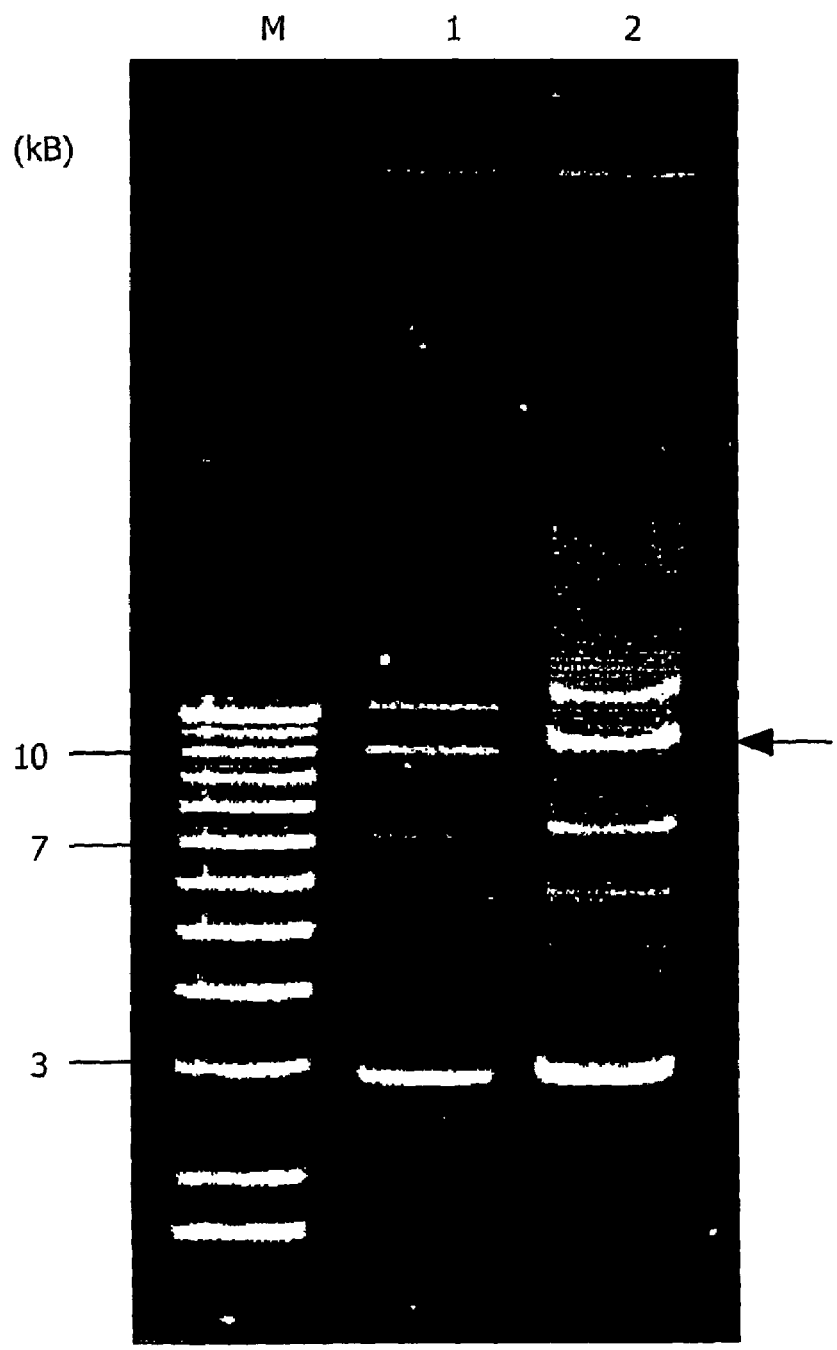
FIG. 10 shows a photograph of the gel electrophoretic pattern obtained in Example 8, in which cDNA cloning was done by the Rec A three-strand formation reaction.

Plasmid pBluescript (SK+) cleaved by NotI and SalI was used as the vector DNA. Furthermore, both ends were protruded using exonuclease III. Specifically, 100 µl of an exonuclease reaction solution (50 mM Tris-HCl, pH8.0, 5 mM MgCl$_2$, 10 mM 2-mercaptoetanol, and 180 unit exonuclease III) containing 300 ng of the DNA, in which the 5' end was protruded with restriction enzymes NotI and SalI, was reacted at 37° C. for 1 min. The DNA was concentrated and the enzymes de-activated by phenol-chloroform extraction and ethanol precipitation. A 7 kb long rat cDNA (refer to Ohara, O. et al., Brain Res. Mol. Brain Res. 57 (2) 181–192 (1998); GenBank accession No. AB008551) was used as the insert DNA. Both ends of this cDNA, comprised sequences that overlap with the end region of vector DNA, having lengths of 54 bp and 55 bp, respectively. The three-strand formation reaction was done between the aforementioned vector DNA and insert DNA. For the three-strand formation reaction, 200 ng of insert DNA, 6.0 µg of Rec A protein, 4.8 mM ATP-γS, 30 mM Tris-acetate (pH7.2), 1 g of vector DNA, and 21.5 mM magnesium acetate were contained in 40 l of reaction solution. This reaction solution was incubated at 37° C. for 30 min. 0.5% (W/Vol) SDS, and 0.7 mg/ml proteinase K were added, incubated at 37° C. for 30 min, and then 60 µl TE Buffer, (10 mM Tris-HCl, 1 mM EDTA) was added to make a total volume of 100 µl. After doing a single phenol-chloroform extraction, a single chloroform extraction, and ethanol precipitation was done, and the DNA was dissolved in 10 µl distilled water. The whole amount was subjected to 1% agarose gel electrophoresis and the result is shown in lane 1 of FIG. 10. Lane M shows the kb DNA ladder marker. Lane 2 shows the same result as lane 1, other than the fact that the exonuclease reaction was done for 2 min.

Figure shows that complex formation can be seen with the Rec A reaction against exo-treated vector and insert. The exo-treatment may be for one or two minutes. Though the length of the linearized region has not been measured directly, it is assumed to be about 100 to 200 nucleotides per minute.

EXAMPLE 9

The Repair Reaction of Ligated DNA

Figure 11:
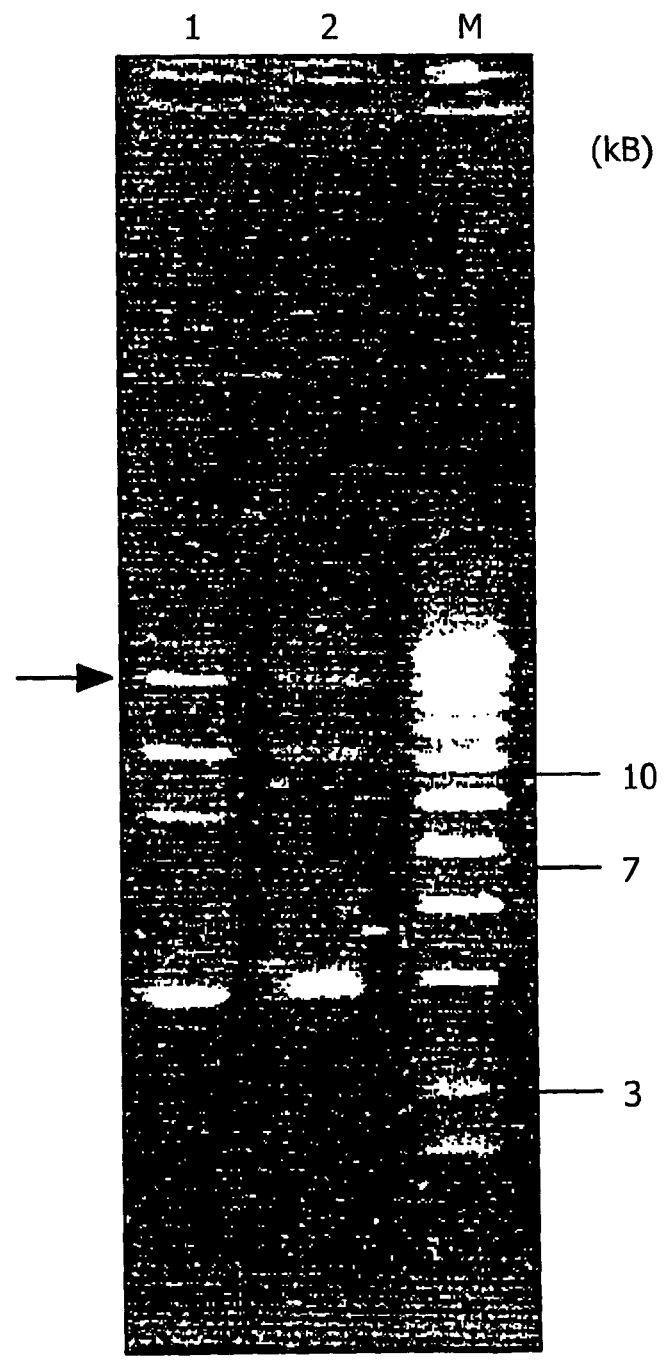
FIG. 11 shows a photograph of the gel electrophoretic pattern obtained in Example 9, in which the effect of the modification reaction of the ligated cDNA complex using modification enzymes was examined by the Rec A three-strand formation reaction.

The sample prior to electrophoresis in the reaction of Example 1, was mixed with T4 DNA Polymerase reaction solution and Klenow reaction solution and incubated at 37° C. for 15 min. T4 DNA Polymerase reaction solution contains, 0.25 mM 4dNTPs, 33 mM Tris-acetate, pH7, 66 mM CH3CK, 10 mM $(CH_3COO)_2Mg$, 0.5 mM DTT, 0.01% BSA, and 4 unit T4 DNA Polymerase. After the reaction, 20 µl TE Buffer solution, (10 mM Tris-$HCl_1$, 1 mM EDTA) was added to make a total volume of 100 µl. A single phenol-chloroform extraction, a single chloroform extraction, and an ethanol precipitation was done to concentrate and isolate the DNA molecules contained. The DNA precipitate was dissolved in 10 µl distilled water. 1.0% agarose gel electrophoresis was carried out for a suitable amount thereof. After electrophoresis, ethidium bromide staining was done, and photographs taken to observe DNA. Lane 1 of FIG. 11, shows the DNA prior to the reaction. Lane 2 shows the results after reacting with T4 DNA Polymerase. Lane M shows the kb DNA ladder marker.

Figure shows that although the band identified near the 6 kb position disappears by the T4 pol. treatment, the vector/insert complex-like-band around 10 kb does not disappear.

EXAMPLE 10

Verification of Ligated DNA

Figure 12:
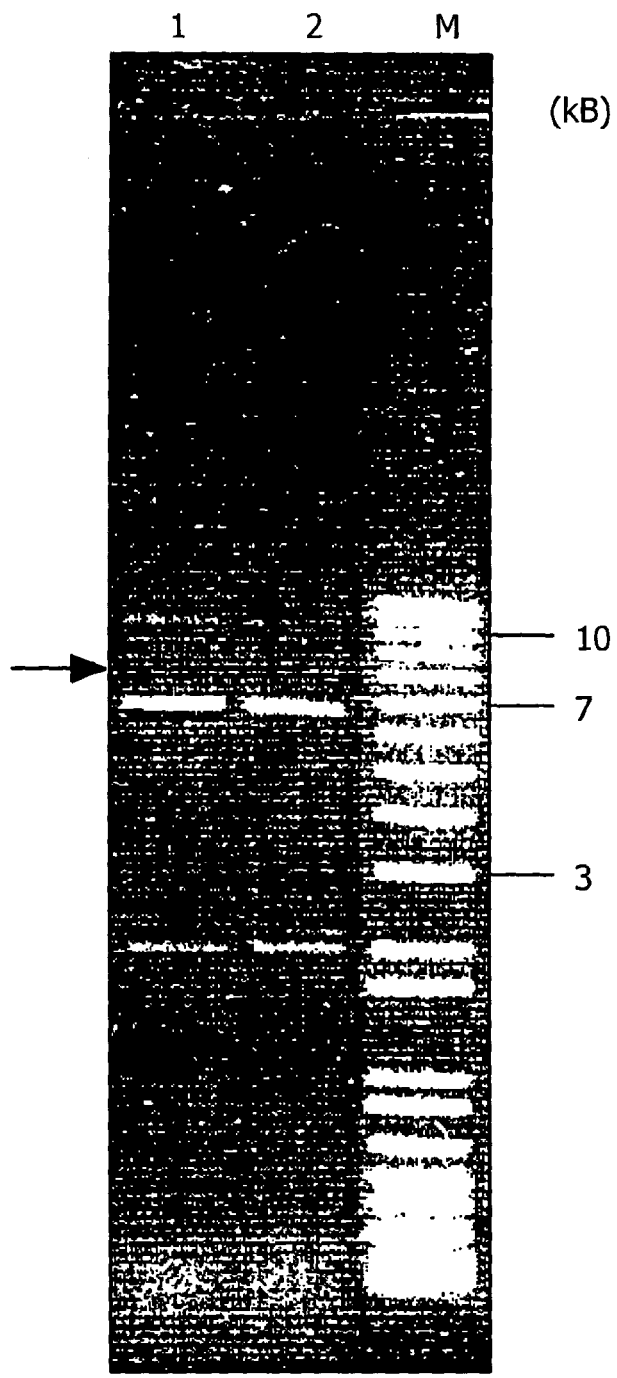
FIG. 12 shows a photograph of the gel electrophoretic pattern obtained in Example 10, in which the ligated cDNA was confirmed by the Rec A three-strand formation reaction.

Results are shown in FIG. 12. Lane M shows the kb DNA ladder marker. Same sample as in lane 1 of FIG. 11 was transformed into E. coli cell line DH10B by the usual electroporation methods. After culturing overnight in an agar medium containing ampicillin, plasmids from the 500 clones on the plate were collected, and agarose gel electrophoresis was performed. The result is shown in lane 1. Lane 2 shows the results for the same sample as in lane 2 of FIG. 11, to which the same treatment as lane 1 has been given.

Figure shows that DNA has been cloned even after T4 pol. treatment.

EXAMPLE 11

The Effect of Endonuclease Treatment on the DNA Ligation Complex

Prior to the transformation of the ligated DNA (having the three-stranded structure partially) into E. coli, it was treated with various endonucleases, and the change in the efficiency of transformation that followed, was examined. The DNA complex ligated by the three-strand formation according to the method of Example 1 was subjected to, experiment 1: Cleavase (R) (Third Wave Technologies, Inc.) reaction (mixed with a reaction solution (composition unknown), the total volume is made to 20 µl, and incubated at 54° C. for 60 min), experiment 2: Munc Bean Nuclease reaction (mixed into a S1 nuclease reaction solution containing 30 units Munc Bean Nuclease (TaKaRa), 30 mM sodium acetate (pH5.0), 100 mM NaCl, 1 mM $(CH_3COO)_2Zn$, and 5% glycerol, total volume made to 20 µl, and incubated at 37° C. for 30 min), experiment 3: S1 nuclease reaction (mixed into a S1 nuclease reaction solution containing 10 units S1 Nuclease (TaKaRa), 30 mM sodium acetate (pH 4.6), 280 mM NaCl, 1 mM $ZnSO_4$, the total volume is made to 20 µl, and incubated at 3° C. for 10 min), experiment 4: BAL31 nuclease reaction (mixed into a BAL31 nuclease reaction solution containing 10 units BAL31 nuclease (TaKaRa), 20 mM Tris-HCl (pH8.0), 600 mM NaCl, 12 mM $CaCl_2$, 12 mM $MgCl_2$, and 1 mM EDTA, the total volume is made to 20 µl, and incubated at 20° C. for 30 min), and experiment 5: no treatment. After reacting the DNA ligate complex with the above various types of enzymes, 80 µl of TE Buffer solution (10 mM Tris-HCl, 1 mM EDTA) was added to make a total volume of 100 µl. After doing a single phenol-chloroform extraction, and a single chloroform extraction, ethanol precipitation was done, and resulting DNA was dissolved in 10 µl distilled water. 2 ml thereof was transformed to E. coli cell line DH10B by the usual electroporation. After culturing overnight in an agar medium containing ampicillin, IPTG, and X-Gal, the resulting white-colonies containing insert DNA was counted. Table 2 shown below depicts the results.

Based on this data, the transformation efficiency of each experiment was estimated and is shown below in Table 3.

TABLE 2

| | Experiment no. | | | | |
|---|---|---|---|---|---|
| | 1 | 2 | 3 | 4 | 5 |
| Number of white-colonies | 335 | 206 | 153 | 164 | 82 |

TABLE 3

The transformation efficiency of the modification enzymes used in the treatments

| | |
|---|---|
| Cleavase (R) (Third Wave Technologies) | $3.4 \times 10^7$ cfu/µg vector |
| Munc Bean Nuclease (TaKaRa) | $2.1 \times 10^7$ cfu/µg vector |
| S1 nuclease (TaKaRa) | $1.5 \times 10^7$ cfu/µg vector |
| BAL31 nuclease (TaKaRa) | $1.6 \times 10^7$ cfu/µg vector |
| No treatment | $8.2 \times 10^6$ cfu/µg vector |

Tables 2 and 3 confirm that transformation efficiency can be improved by treating with an exonuclease prior to the transformation.

EXAMPLE 12 cDNA Ligation by the Rec A Reaction

Figure 13A:
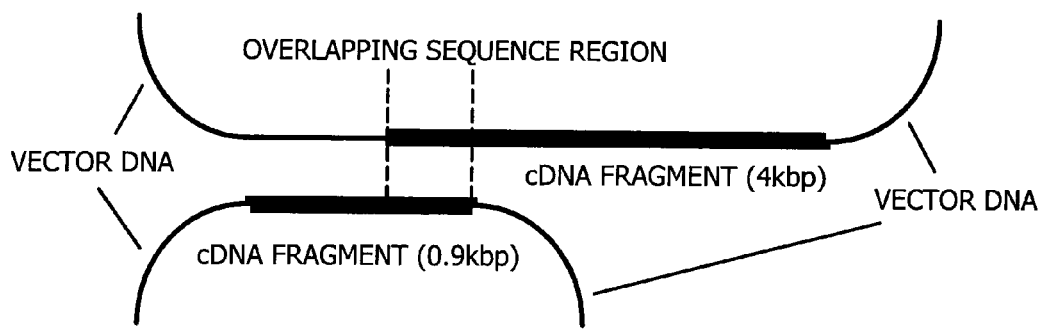
As shown in FIG. 13(A), a 4 kb and a 0.9 kb cDNA sequence have overlapping common sequences.
Figure 13B:
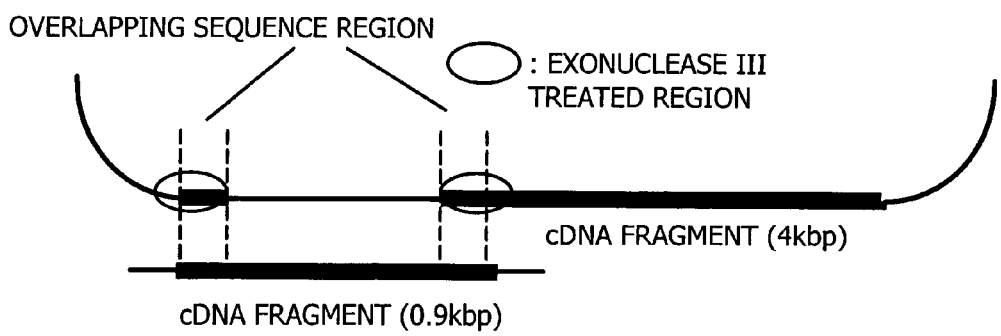
In FIG. 13(B), the 0.9 kb cDNA and the 4.0 kb cDNAs were treated with exonuclease III and restriction enzymes and ligated to one another resulting in a 4.9 kb cDNA product as shown in FIG. 13(C).
Figure 13C:
FIG. 13 shows a diagram of the reaction in Example 12, in which the ligation of a 4 kb cDNA and a 0.9 kb cDNA was done by the Rec A three-stranded formation reaction.

An approximately 4 kbp-long human brain cDNA (a cDNA comprising the chicken myosin-like sequence; Gen-Bank accession No. AB023217) and a 0.9 kbp cDNA prepared based on its 5' end sequence by the 5'-RACE method were ligated by the Rec A reaction. The reaction strategy is shown in FIG. 13. As shown in FIG. 13 (A), the 4 kbp cDNA and the 0.9 kbp cDNA have overlapping common sequences. As shown in FIG. 13 (B), 0.9 kbp cDNA was excused from the vector by restriction enzyme NotI/

SaII and 4 kbp cDNA was treated with SaII and exonuclease III, and then, the ligation reaction was done between these cDNAs. A 4.9 kbp cDNA was obtained as the final product of the reaction, as shown in FIG. 13 (C).

The specific details of the reaction are as follows. For the 4 kbp cDNA cloned to the restriction enzyme NotI/SaII site, that which has been cleaved by the restriction enzyme SaII was used. This results in a 4 kbp cDNA cleaved at the 5' end. Furthermore, using exonuclease III, both ends were 5' protruded-ended. Specifically, 100 µl of an exonuclease reaction solution (50 mM Tris-HCl, pH8.0, 5 mM MgCl$_2$, 10 mM 2-mercaptoethanol, and 180 unit exonuclease III) containing 1000 ng of the DNA, was reacted at 37° C. for 1 min. The DNA was concentrated and the enzymes were de-activated by phenol-chloroform extraction and ethanol precipitation. 0.9 kbp cDNA was prepared based on by the 5'-RACE method using Superscript Plasmid System (Gibco BRL), and then, the 0.9 kbp cDNA, which was subcloned to plasmid pBluescript (SK+), was excised with restriction enzyme BssHII. In both ends of this cDNA, an approximately 50 bp-long, additional sequence is present. The ligation reaction of the above two cDNAs was done as follows. In the three-strand formation reaction, 401 of the reaction solution contains, 200 ng of 0.9 kb cDNA, 600 ng of 4 kbp cDNA, 6.0 µg of Rec A protein, 4.8 mM ATP-γS, 30 mM Tris-acetate (pH7.2), 1 g target DNA, and 21.5 mM magnesium acetate. Next, 0.5% (W/Vol) SDS, and 0.7 mg/ml proteinase K were added, was incubated at 37° C. for 30 min, and then 60 µl TE Buffer solution (10 mM Tris-HCl, 1 mM EDTA) was added to make a total volume of 100 µl. After a single phenol-chloroform extraction and a single chloroform extraction, followed by an ethanol precipitation, the resulting DNA was dissolved in 10 µl distilled water. 2 µl thereof was transformed into *E. Coli* cell line DH10B. Then after an overnight culture in an agar medium containing ampicillin, the nucleotide sequence of the plasmid DNA contained in the resulting colonies was examined.

As a result of examining 30 colonies having insert DNA-comprising plasmids, a plasmid having the objective ligated DNA insert, in which the 0.9 kbp cDNA and the 4 kbp cDNA were ligated, was obtained.

---

SEQUENCE LISTING

<160> NUMBER OF SEQ ID NOS: 14

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:synthesized
    by referring to the random sequence 13mer that does not contain T,
    and the following sequence of one end of the exon 11 region of p53
    gene within the human genomic DNA

<400> SEQUENCE: 1
gacgacgaca agacacctga agtccaaaaa gggtcagtc                          39

<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence:synthesized
    by referring to the random sequence 14mer that does not contain T,
    and the following sequence of one end of the exon 11 region of p53
    gene within the human genomic DNA

<400> SEQUENCE: 2
gaggagaagc ccggtggcag caaagttta ttgtaaaata                          40

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:synthesized
    by referring to the sequence of one end of the exon 11 region of
    p53 gene within the human genomic DNA

<400> SEQUENCE: 3
cacctgaagt ccaaaaggg tcagtc                                         26

<210> SEQ ID NO 4
<211> LENGTH: 26
<212> TYPE: DNA

```
<213> ORGANISM: Artificial Sequence
<220> FEATURE:
<223> OTHER INFORMATION: Description of Artificial Sequence:synthesized
      by referring to the sequence of one end of the exon 11 region of
      p53 gene within the human genomic DNA

<400> SEQUENCE: 4
tggcagcaaa gttttattgt aaaata                                          26

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:synthesized
      by referring to the nucleotide sequence in the proximity of SnaBI
      recognition site of M13mp18RF

<400> SEQUENCE: 5
agaggctttg aggactaaag acttttttcat gaggaagttt ccattaaacg ggtaaaatac     60

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence:synthesized
      by referring to the nucleotide sequence in the proximity of SnaBI
      recognition site of M13mp18RF

<400> SEQUENCE: 6
gtattttacc cgtttaatgg aaacttcctc atgaaaaagt ctttagtcct caaagcctct     60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence:synthesized
      by referring to the nucleotide sequence in the proximity of ScaI
      recognition site of pBR322

<400> SEQUENCE: 7
cactgcataa ttctcttact gtcatgccat ccgtaagatg cttttctgtg actggtgagt     60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence:synthesized
      by referring to the nucleotide sequence in the proximity of SnaBI
      recognition site of M13mp18RF

<400> SEQUENCE: 8
tgttttagtg tattctttcg cctctttcgt tttaggttgg tgccttcgta gtggcattac     60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:synthesized
      by referring to the nucleotide sequence in the proximity of SnaBI
      recognition site of M13mp18RF

<400> SEQUENCE: 9
gtaatgccac tacgaaggca ccaacctaaa acgaaagagg cgaaagaata cactaaaaca     60
```

-continued

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:synthesized
      by referring to the end sequence of DNA obtained by cleaving
      M13mp18RF with SnaBI

<400> SEQUENCE: 10 acttttcat gaggaagttt ccattaaacg ggtaaaatac                    40

<210> SEQ ID NO 11
<211> LENGTH: 23
<212> TYPE: DNA
<213> ORGANISM: Artificial Sequence
<220> FEATURE:
<223> OTHER INFORMATION: Description of double stranded sequence
      (DNA 1) recited in Figure 1.

<400> SEQUENCE: 11
ctagtatcgg acgacgacaa gat                                     23

<210> SEQ ID NO 12
<211> LENGTH: 23
<212> TYPE: DNA
<213> ORGANISM: Artificial Sequence
<220> FEATURE:
<223> OTHER INFORMATION: Description of double stranded sequence
      (DNA 2) recited in Figure 1. The sequence from nucleotide numbers
      15 to 23 is double stranded.

<400> SEQUENCE: 12
gacgacgaca agatgatcat gat                                     23

<210> SEQ ID NO 13
<211> LENGTH: 32
<212> TYPE: DNA
<213> ORGANISM: Artificial Sequence
<220> FEATURE:
<223> OTHER INFORMATION: Description of double stranded sequence
      (DNA (1+2)) recited in Figure 1.

<400> SEQUENCE: 13
ctagtatcgg acgacgacaa gatgatcatg at                           32

<210> SEQ ID NO 14
<211> LENGTH: 10
<212> TYPE: DNA
<213> ORGANISM: Artificial Sequence
<220> FEATURE:
<223> OTHER INFORMATION: Description of double stranded sequence recited
      in Figure 2.

<400> SEQUENCE: 14
aaaaaaaaaa                                                    10

What is claimed is:

1. A method of ligating a double-stranded end of a first double-stranded DNA and a single-stranded end of second double-stranded DNA, wherein the method comprises:
   a) contacting, in the presence of a homologous recombination protein, the single-stranded end of said second double-stranded DNA and the double-stranded end of said first double-stranded DNA, wherein the nucleotide sequence of one strand of said first double-stranded end is homologous to the nucleotide sequence of said single-stranded end, to form a three-stranded structure comprising said single-stranded end and said double-stranded end, and
   b) completing the ligation by converting the three-stranded structure into a double-stranded structure by inserting a DNA complex comprising the three-stranded structure into cells and replicating it therein;
wherein the homologous recombination protein is a Rec A protein.

2. The method of ligation of claim 1, wherein said DNA complex is a circular DNA complex having a three-stranded structure in two positions, wherein said three-stranded structures are made by either the ligation of:
   a) a double-stranded DNA comprising a single-stranded region at both ends, and
   b) a double-stranded DNA having at both ends a double-stranded region comprising sequences that are respectively homologous to each single-stranded region in a); or the ligation of:
   c) a double-stranded DNA comprising a single-stranded region at one end and a double-stranded region at the other end, and
   d) a double-stranded DNA comprising a double-stranded region at one end having a sequence that is homologous to the nucleotide sequence of said single-stranded region in c) and a single-stranded region at the other end comprising a sequence that is homologous to the nucleotide sequence of the double-stranded nucleotide region in c).

3. The method of ligation of claim 2, wherein the nucleotide sequences of the two single-stranded regions in a) are mutually non-complementary.

4. The method of ligation of claim 1, wherein the nucleotide sequence of the single-stranded region is at least a six-mer.

5. The method of claim 1, wherein the step of contacting in part (a) is done furthermore under the presence of nucleoside triphosphate or a derivative thereof.

6. The method of ligation of claim 1, wherein the insertion of the DNA complex comprising a three-stranded structure into cells is done by electroporation.

7. The method of ligation of claim 1, wherein steps a) and b) take place in the absence of DNA ligase.

8. The method of ligation of claim 1, wherein the double-stranded structure resulting from step b) has no gaps.

9. A gene-cloning kit consisting essentially of the following components:
   a) a double-stranded DNA comprising single-stranded regions at both ends, wherein the nucleotide sequences of these single-stranded regions are mutually non-complementary;
   b) an oligonucleotide primer comprising as a part of the 5' end sequence, a sequence that is complementary to one single-stranded region of the nucleotide sequence of (a), and further comprising a sequence that is complementary to a part of one end of a sequence of a gene to be cloned;
   c) an oligonucleotide primer comprising as a part of the 5' end sequence, a sequence that is complementary to the other single-stranded region of the nucleotide sequence of (a), and further comprising a sequence that is complementary to a part of the other end of the sequence of the gene to be cloned; and
   d) a homologous recombination protein;
wherein the homologous recombination protein is a Rec A protein.

10. The kit of claim 9, wherein the nucleotide sequence of each single-stranded region is at least six-mer.

* * * * *